(12) United States Patent
Demmy

(10) Patent No.: US 9,936,952 B2
(45) Date of Patent: Apr. 10, 2018

(54) INTRODUCER ASSEMBLY FOR A SURGICAL FASTENER APPLYING APPARATUS

(71) Applicant: Covidien LP, Mansfield, MA (US)

(72) Inventor: Todd Demmy, Buffalo, NY (US)

(73) Assignee: Covidien LP, Mansfield, MA (US)

( * ) Notice: Subject to any disclaimer, the term of this patent is extended or adjusted under 35 U.S.C. 154(b) by 408 days.

(21) Appl. No.: 14/170,886

(22) Filed: Feb. 3, 2014

(65) Prior Publication Data

US 2015/0216528 A1 Aug. 6, 2015

(51) Int. Cl.
| | | |
|---|---|---|
| A61B 17/00 | (2006.01) | |
| A61B 17/072 | (2006.01) | |
| A61B 17/29 | (2006.01) | |
| A61B 17/32 | (2006.01) | |
| A61B 90/00 | (2016.01) | |
| A61B 90/30 | (2016.01) | |

(52) U.S. Cl.
CPC ...... *A61B 17/07207* (2013.01); *A61B 90/361* (2016.02); *A61B 2017/00477* (2013.01); *A61B 2017/00862* (2013.01); *A61B 2017/07214* (2013.01); *A61B 2017/07257* (2013.01); *A61B 2017/07271* (2013.01); *A61B 2017/2908* (2013.01); *A61B 2017/2926* (2013.01); *A61B 2017/320044* (2013.01); *A61B 2090/304* (2016.02)

(58) Field of Classification Search
CPC ............ A61B 17/32; A61B 17/320092; A61B 17/3205; A61B 17/3209; A61B 17/3211; A61B 17/3213; A61B 17/34; A61B 17/3417; A61B 17/50; A61B 2017/320044; A61B 2017/320072; A61B 2017/3454; A61B 17/29; A61B 17/30
See application file for complete search history.

(56) References Cited

U.S. PATENT DOCUMENTS

| | | |
|---|---|---|
| 2,887,111 A | 5/1959 | Diaz |
| 3,079,606 A | 3/1963 | Bobrov et al. |
| 3,490,675 A | 1/1970 | Green et al. |
| 4,429,695 A | 2/1984 | Green |
| 4,505,414 A | 3/1985 | Filipi |
| 4,545,373 A | 10/1985 | Christoudias |
| 4,589,413 A | 5/1986 | Malyshev et al. |
| 4,602,634 A | 7/1986 | Barkley |
| 4,608,981 A | 9/1986 | Rothfuss et al. |
| 4,610,383 A | 9/1986 | Rothfuss et al. |
| 4,633,861 A | 1/1987 | Chow et al. |

(Continued)

FOREIGN PATENT DOCUMENTS

WO 2004096057 A2 11/2004

OTHER PUBLICATIONS

Extended European Search Report from Appl. No. EP 14199665.2 dated Sep. 18, 2015.

*Primary Examiner* — Melanie Tyson

(57) ABSTRACT

An introducer assembly can be releasably coupled to a surgical instrument and includes a collar, a tip, and an elongated body portion disposed between the collar and the tip. The tip may be configured to releasably engage a dissecting device. The collar may releasably couple the introducer assembly to a shaft of a surgical fastener applying apparatus. The tip may have an opening to receive a distal-most end of an end effector of a surgical fastener applying apparatus.

10 Claims, 13 Drawing Sheets

(56) References Cited

U.S. PATENT DOCUMENTS

| | | |
|---|---|---|
| 4,633,874 A | 1/1987 | Chow et al. |
| 4,671,445 A | 6/1987 | Barker et al. |
| 4,703,887 A | 11/1987 | Clanton et al. |
| 4,728,020 A | 3/1988 | Green et al. |
| 4,784,137 A | 11/1988 | Kulik et al. |
| 4,815,465 A | 3/1989 | Alvarado |
| 4,863,088 A | 9/1989 | Redmond et al. |
| 4,873,977 A | 10/1989 | Avant et al. |
| 4,892,244 A | 1/1990 | Fox et al. |
| 4,991,764 A | 2/1991 | Mericle |
| 5,040,715 A | 8/1991 | Green et al. |
| 5,047,039 A | 9/1991 | Avant et al. |
| 5,065,929 A | 11/1991 | Schulze et al. |
| 5,074,454 A | 12/1991 | Peters |
| 5,083,695 A | 1/1992 | Foslien et al. |
| 5,108,403 A | 4/1992 | Stern |
| 5,111,987 A | 5/1992 | Moeinzadeh et al. |
| 5,129,570 A | 7/1992 | Schulze et al. |
| 5,141,144 A | 8/1992 | Foslien et al. |
| 5,156,633 A | 10/1992 | Smith |
| 5,170,925 A | 12/1992 | Madden et al. |
| 5,217,460 A | 6/1993 | Knoepfler |
| 5,219,354 A | 6/1993 | Choudhury et al. |
| 5,234,454 A | 8/1993 | Bangs |
| RE34,519 E | 1/1994 | Fox et al. |
| 5,281,236 A | 1/1994 | Bagnato et al. |
| 5,282,807 A | 2/1994 | Knoepfler |
| 5,307,976 A | 5/1994 | Olson et al. |
| 5,312,023 A | 5/1994 | Green et al. |
| 5,318,221 A | 6/1994 | Green et al. |
| 5,326,013 A | 7/1994 | Green et al. |
| 5,332,142 A | 7/1994 | Robinson et al. |
| 5,364,003 A | 11/1994 | Williamson, IV |
| 5,376,095 A | 12/1994 | Ortiz |
| 5,381,943 A | 1/1995 | Allen et al. |
| 5,383,880 A | 1/1995 | Hooven |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,407,293 A | 4/1995 | Crainich |
| 5,415,334 A | 5/1995 | Williamson et al. |
| 5,415,335 A | 5/1995 | Knodell, Jr. |
| 5,417,361 A | 5/1995 | Williamson, IV |
| 5,425,745 A | 6/1995 | Green et al. |
| 5,431,323 A | 7/1995 | Smith et al. |
| 5,433,721 A | 7/1995 | Hooven et al. |
| 5,447,265 A | 9/1995 | Vidal et al. |
| 5,452,837 A | 9/1995 | Williamson, IV et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,474,566 A | 12/1995 | Alesi et al. |
| 5,476,206 A | 12/1995 | Green et al. |
| 5,484,451 A | 1/1996 | Akopov et al. |
| 5,485,947 A | 1/1996 | Olson et al. |
| 5,487,500 A | 1/1996 | Knodel et al. |
| 5,489,058 A | 2/1996 | Plyley et al. |
| 5,501,654 A | 3/1996 | Failla et al. |
| 5,507,426 A | 4/1996 | Young et al. |
| 5,507,754 A | 4/1996 | Green et al. |
| 5,518,163 A | 5/1996 | Hooven |
| 5,518,164 A | 5/1996 | Hooven |
| 5,522,788 A | 6/1996 | Kuzmak |
| 5,527,298 A | 6/1996 | Vance et al. |
| 5,529,235 A | 6/1996 | Boiarski et al. |
| 5,531,744 A | 7/1996 | Nardella et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,551,622 A | 9/1996 | Yoon |
| 5,553,765 A | 9/1996 | Knodel et al. |
| 5,562,239 A | 10/1996 | Boiarski et al. |
| 5,562,241 A | 10/1996 | Knodel et al. |
| 5,562,682 A | 10/1996 | Oberlin et al. |
| 5,564,615 A | 10/1996 | Bishop et al. |
| 5,573,543 A | 11/1996 | Akopov et al. |
| 5,577,654 A | 11/1996 | Bishop |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,649,957 A | 7/1997 | Levin |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,665,097 A | 9/1997 | Baker et al. |
| 5,665,100 A | 9/1997 | Yoon |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,680,982 A | 10/1997 | Schulze et al. |
| 5,690,269 A | 11/1997 | Bolanos et al. |
| 5,690,653 A | 11/1997 | Richardson et al. |
| 5,692,668 A | 12/1997 | Schulze et al. |
| 5,697,542 A | 12/1997 | Knodel et al. |
| 5,704,534 A | 1/1998 | Huitema et al. |
| 5,709,334 A | 1/1998 | Sorrentino et al. |
| 5,711,472 A | 1/1998 | Bryan |
| 5,713,505 A | 2/1998 | Huitema |
| 5,716,366 A | 2/1998 | Yates |
| 5,728,110 A | 3/1998 | Vidal et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,766,187 A | 6/1998 | Sugarbaker |
| 5,769,303 A | 6/1998 | Knodel et al. |
| 5,772,099 A | 6/1998 | Gravener |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |

(56) References Cited

U.S. PATENT DOCUMENTS

| | | | |
|---|---|---|---|
| 5,862,972 A | 1/1999 | Green et al. | |
| 5,865,361 A | 2/1999 | Milliman et al. | |
| 5,871,135 A | 2/1999 | Williamson, IV et al. | |
| 5,897,562 A | 4/1999 | Bolanos et al. | |
| 5,901,895 A | 5/1999 | Heaton et al. | |
| 5,908,427 A | 6/1999 | McKean et al. | |
| 5,911,353 A | 6/1999 | Bolanos et al. | |
| 5,918,791 A | 7/1999 | Sorrentino et al. | |
| 5,941,442 A | 8/1999 | Geiste et al. | |
| 5,954,259 A | 9/1999 | Viola et al. | |
| 6,001,120 A | 12/1999 | Levin | |
| 6,004,335 A | 12/1999 | Vaitekunas et al. | |
| 6,010,054 A | 1/2000 | Johnson et al. | |
| 6,013,028 A | 1/2000 | Jho et al. | |
| 6,032,849 A | 3/2000 | Mastri et al. | |
| 6,036,714 A | 3/2000 | Chin | |
| 6,079,606 A | 6/2000 | Milliman et al. | |
| 6,099,537 A | 8/2000 | Sugai et al. | |
| 6,099,551 A | 8/2000 | Gabbay | |
| 6,106,539 A * | 8/2000 | Fortier | A61B 17/3417 604/164.06 |
| 6,109,500 A | 8/2000 | Alli et al. | |
| 6,165,183 A | 12/2000 | Kuehn et al. | |
| 6,202,914 B1 | 3/2001 | Geiste et al. | |
| 6,202,917 B1 | 3/2001 | Weaver et al. | |
| 6,241,139 B1 | 6/2001 | Milliman et al. | |
| 6,241,740 B1 | 6/2001 | Davis et al. | |
| 6,250,532 B1 | 6/2001 | Green et al. | |
| 6,264,086 B1 | 7/2001 | McGuckin, Jr. | |
| 6,264,087 B1 | 7/2001 | Whitman | |
| 6,269,977 B1 | 8/2001 | Moore | |
| 6,315,183 B1 | 11/2001 | Piraka | |
| 6,315,184 B1 | 11/2001 | Whitman | |
| 6,325,810 B1 | 12/2001 | Hamilton et al. | |
| 6,330,965 B1 | 12/2001 | Milliman et al. | |
| 6,439,446 B1 | 8/2002 | Perry et al. | |
| 6,443,970 B1 | 9/2002 | Schulze et al. | |
| 6,443,973 B1 | 9/2002 | Whitman | |
| 6,458,128 B1 | 10/2002 | Schulze | |
| 6,464,702 B2 | 10/2002 | Schulze et al. | |
| 6,488,196 B1 | 12/2002 | Fenton, Jr. | |
| 6,503,257 B2 | 1/2003 | Grant et al. | |
| 6,505,768 B2 | 1/2003 | Whitman | |
| 6,506,210 B1 | 1/2003 | Kanner | |
| 6,530,942 B2 | 3/2003 | Fogarty et al. | |
| 6,544,274 B2 | 4/2003 | Danitz et al. | |
| 6,554,829 B2 | 4/2003 | Schulze et al. | |
| 6,554,844 B2 | 4/2003 | Lee et al. | |
| 6,565,554 B1 | 5/2003 | Niemeyer | |
| 6,582,452 B2 | 6/2003 | Coleman et al. | |
| 6,587,750 B2 | 7/2003 | Gerbi et al. | |
| 6,592,581 B2 | 7/2003 | Bowe | |
| 6,592,597 B2 | 7/2003 | Grant et al. | |
| 6,594,552 B1 | 7/2003 | Nowlin et al. | |
| 6,602,252 B2 | 8/2003 | Mollenauer | |
| 6,616,661 B2 | 9/2003 | Wellman et al. | |
| 6,616,686 B2 | 9/2003 | Coleman et al. | |
| 6,620,161 B2 | 9/2003 | Schulze et al. | |
| 6,623,482 B2 | 9/2003 | Pendekanti et al. | |
| 6,652,521 B2 | 11/2003 | Schulze | |
| 6,656,193 B2 | 12/2003 | Grant et al. | |
| 6,679,895 B1 | 1/2004 | Sancoff et al. | |
| 6,685,712 B2 | 2/2004 | Cummins et al. | |
| 6,695,840 B2 | 2/2004 | Schulze | |
| 6,698,643 B2 | 3/2004 | Whitman | |
| 6,722,552 B2 | 4/2004 | Fenton, Jr. | |
| 6,755,815 B2 | 6/2004 | Schultz | |
| 6,761,725 B1 | 7/2004 | Grayzel et al. | |
| 6,767,356 B2 | 7/2004 | Kanner et al. | |
| 6,773,435 B2 | 8/2004 | Schulze et al. | |
| 6,773,439 B2 | 8/2004 | George et al. | |
| 6,773,444 B2 | 8/2004 | Messerly | |
| 6,790,217 B2 | 9/2004 | Schulze et al. | |
| 6,821,273 B2 | 11/2004 | Mollenauer | |
| 6,905,057 B2 | 6/2005 | Swayze et al. | |
| 6,926,731 B2 | 8/2005 | Coleman et al. | |
| 6,951,568 B1 | 10/2005 | Chin | |
| 6,976,969 B2 | 12/2005 | Messerly | |
| 7,041,099 B2 | 5/2006 | Thomas et al. | |
| 7,063,699 B2 | 6/2006 | Hess et al. | |
| 7,131,978 B2 | 11/2006 | Sancoff et al. | |
| 7,147,138 B2 | 12/2006 | Shelton, IV | |
| 7,300,444 B1 | 11/2007 | Nielsen et al. | |
| 7,308,998 B2 | 12/2007 | Mastri et al. | |
| 7,364,060 B2 | 4/2008 | Milliman | |
| 7,396,356 B2 | 7/2008 | Mollenauer | |
| 7,404,508 B2 | 7/2008 | Smith et al. | |
| 7,419,080 B2 | 9/2008 | Smith et al. | |
| 7,500,979 B2 | 3/2009 | Hueil et al. | |
| 7,556,186 B2 | 7/2009 | Milliman | |
| 7,857,187 B2 | 12/2010 | Milliman | |
| 7,866,523 B1 | 1/2011 | White et al. | |
| 8,136,711 B2 | 3/2012 | Beardsley et al. | |
| 8,348,123 B2 | 1/2013 | Scirica et al. | |
| 2001/0034535 A1 | 10/2001 | Schultz | |
| 2002/0069884 A1 | 6/2002 | Boyd et al. | |
| 2002/0074004 A1 | 6/2002 | Boyd et al. | |
| 2003/0065351 A1 | 4/2003 | Hess et al. | |
| 2004/0019355 A1 | 1/2004 | Mehdizadeh | |
| 2004/0236326 A1 | 11/2004 | Schulze et al. | |
| 2004/0243151 A1 | 12/2004 | Demmy et al. | |
| 2005/0022601 A1 | 2/2005 | Blakley | |
| 2005/0080434 A1 | 4/2005 | Chung et al. | |
| 2005/0096670 A1 | 5/2005 | Wellman et al. | |
| 2005/0096671 A1 | 5/2005 | Wellman et al. | |
| 2005/0119669 A1 | 6/2005 | Demmy | |
| 2005/0216055 A1 | 9/2005 | Scirica et al. | |
| 2005/0216057 A1 | 9/2005 | Coleman et al. | |
| 2006/0151568 A1 | 7/2006 | Weller et al. | |
| 2006/0208028 A1 | 9/2006 | Kanner | |
| 2007/0149993 A1 | 6/2007 | Kasahara et al. | |
| 2007/0187455 A1 | 8/2007 | Demmy et al. | |
| 2007/0221700 A1 | 9/2007 | Ortiz et al. | |
| 2007/0221701 A1 | 9/2007 | Ortiz et al. | |
| 2008/0237297 A1 * | 10/2008 | Demmy | A61B 17/07207 227/176.1 |
| 2008/0249565 A1 | 10/2008 | Michler et al. | |
| 2008/0269793 A1 | 10/2008 | Scirica et al. | |
| 2008/0269801 A1 | 10/2008 | Coleman et al. | |
| 2008/0269802 A1 | 10/2008 | Coleman et al. | |
| 2008/0272173 A1 | 11/2008 | Coleman et al. | |
| 2009/0069806 A1 | 3/2009 | De La Mora Levy et al. | |
| 2010/0094315 A1 | 4/2010 | Beardsley et al. | |
| 2010/0100045 A1 * | 4/2010 | Pravongviengkham | A61B 17/3421 604/164.09 |
| 2011/0101065 A1 | 5/2011 | Milliman | |
| 2012/0143218 A1 | 6/2012 | Beardsley et al. | |
| 2015/0065804 A1 * | 3/2015 | Kleyman | A61B 17/3417 600/204 |
| 2015/0083776 A1 * | 3/2015 | Lim | A61B 17/07207 227/175.1 |

* cited by examiner

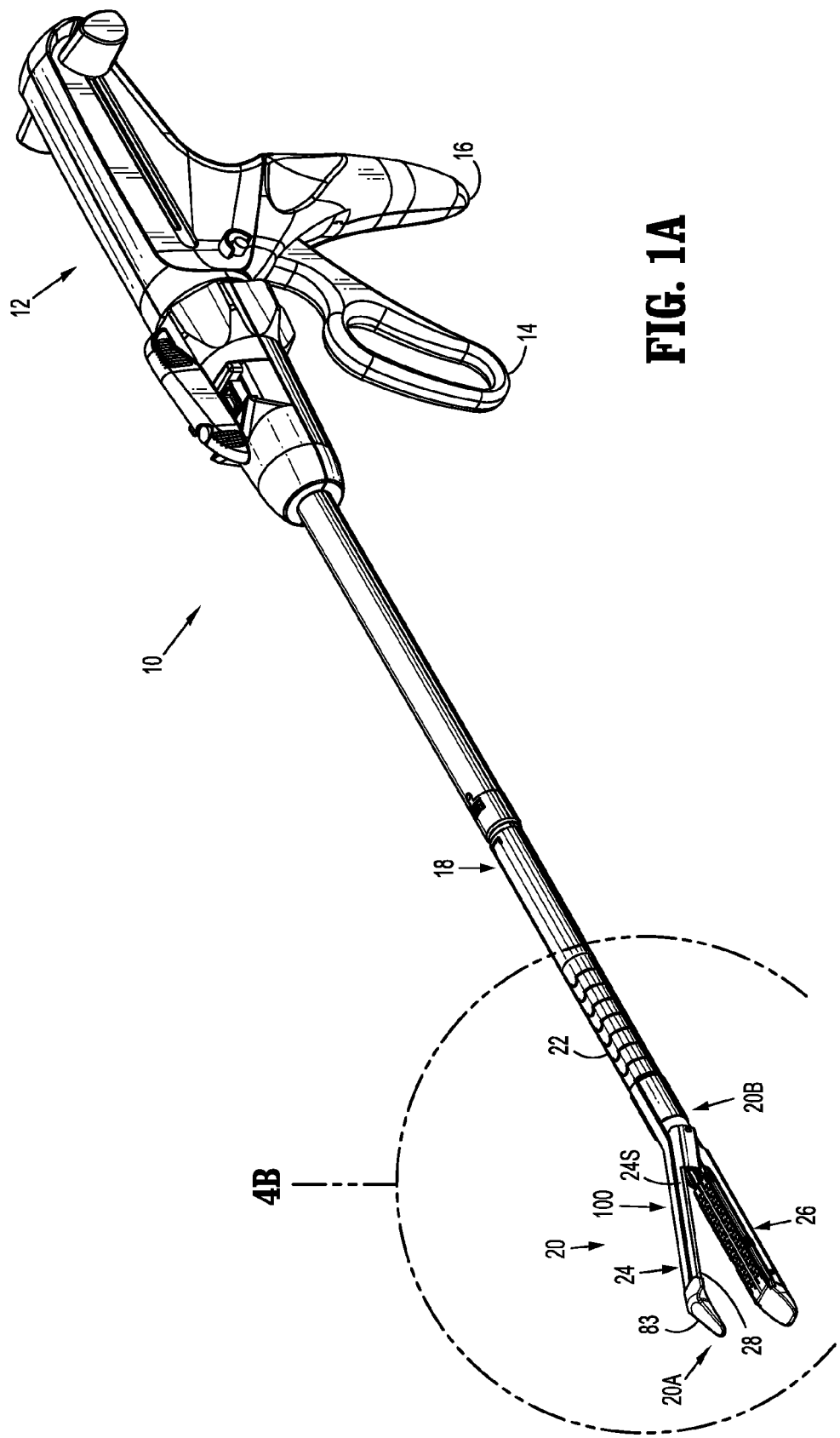

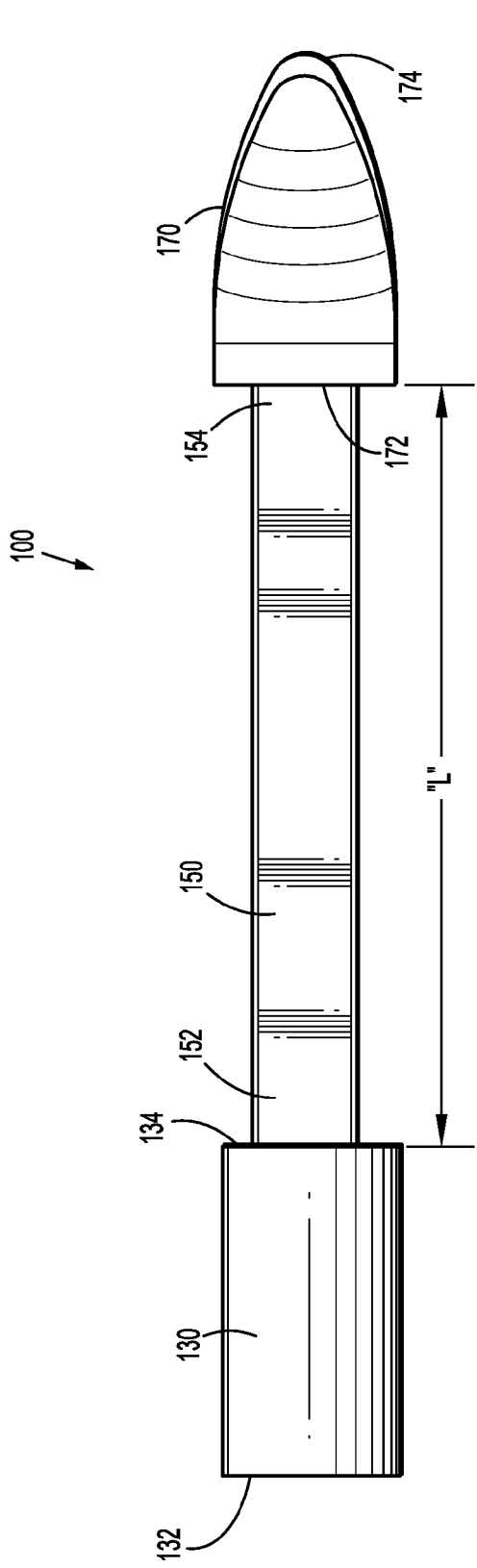
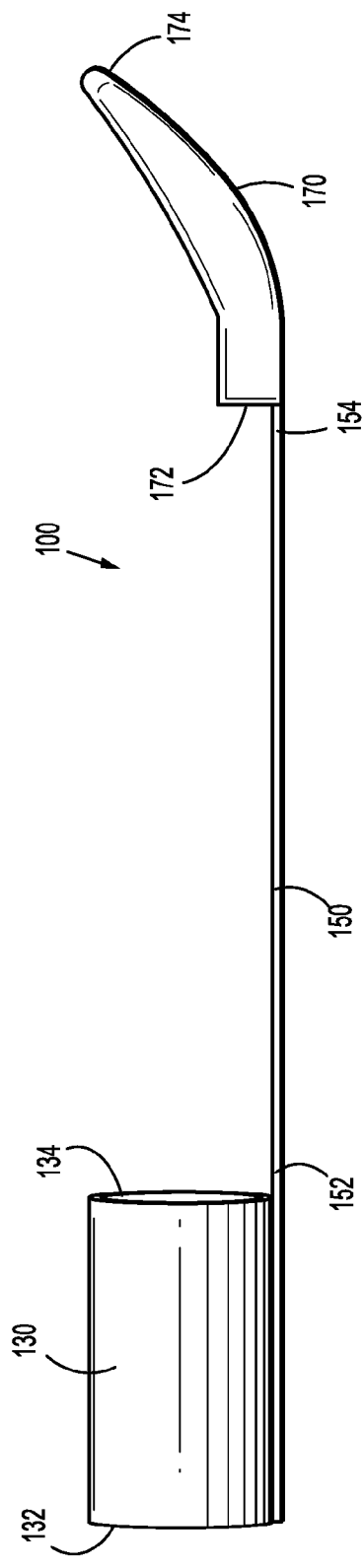

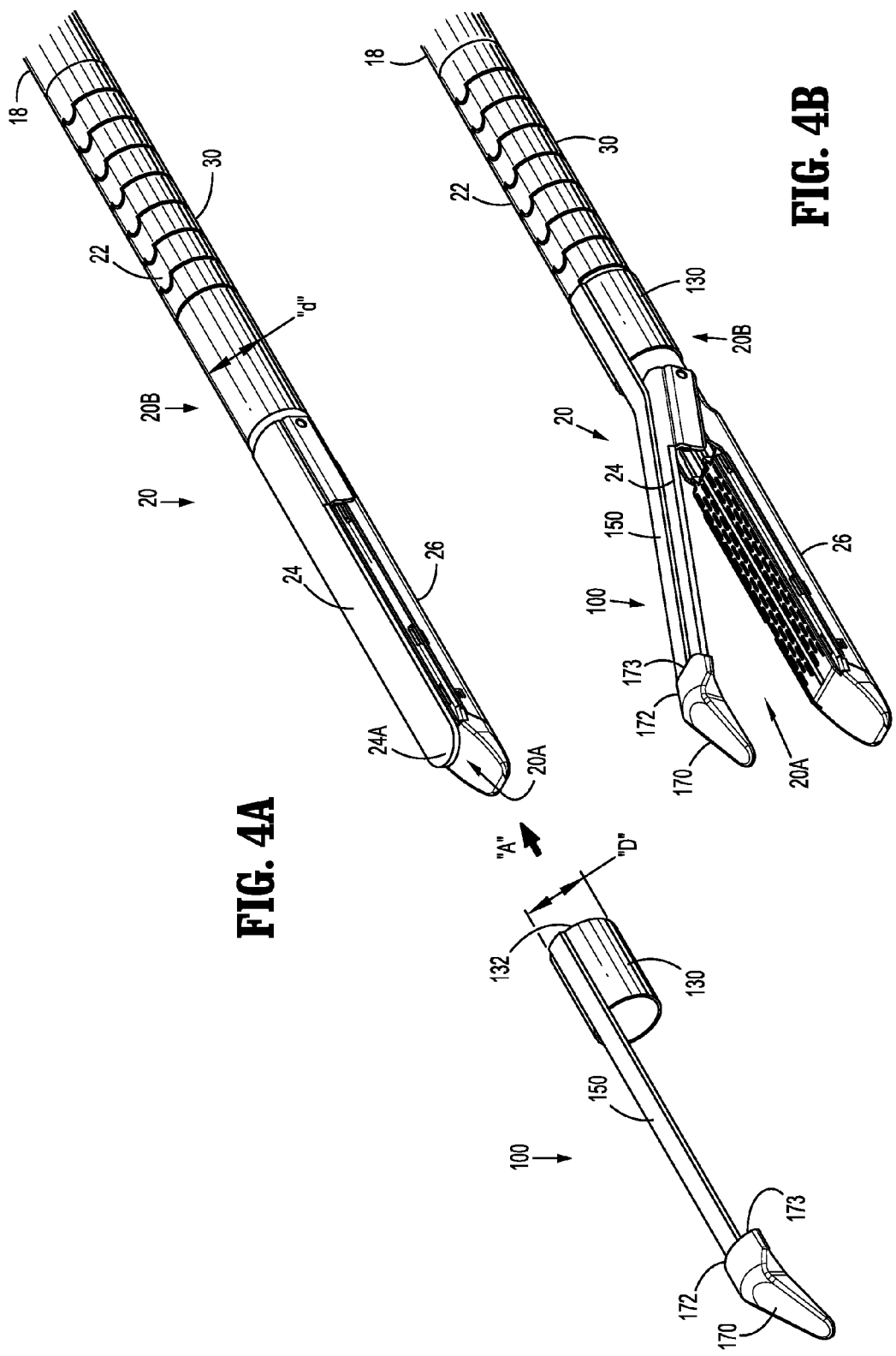

INTRODUCER ASSEMBLY FOR A SURGICAL FASTENER APPLYING APPARATUS

BACKGROUND

1. Technical Field

The present disclosure relates generally to an apparatus for the application of surgical fasteners to tissue. More specifically, the present disclosure relates to an introducer assembly for use with a surgical fastener applying apparatus to facilitate the separation of tissue and access to internal anatomical structures.

2. Background of the Related Art

In an effort to reduce trauma and recovery time, many surgical procedures are performed through small openings in the skin, such as an incision or a natural body orifice. Generally, such procedures are referred to as "endoscopic," unless performed on the patient's abdomen, in which case the procedure is referred to as "laparoscopic." Throughout the present disclosure, the term "minimally invasive" should be understood to encompass both endoscopic and laparoscopic procedures.

During the course of minimally invasive surgical procedures, a surgical fastener applying apparatus is often employed. Typically, these surgical fastener applying apparatus include a first member that is movable relative to a second member such that tissue is positionable therebetween to facilitate grasping and/or clamping of the tissue.

Linear surgical fastener applying apparatus generally include two elongated jaw members, one of which includes a surgical fastener cartridge housing a plurality of surgical fasteners that are arranged in two or more linear rows, and the other of which includes an anvil member with a plurality of fastener forming pockets that are configured and dimensioned to receive and form the surgical fasteners upon ejection of the fasteners from the surgical fastener cartridge. Typically, the surgical fastener applying apparatus will also include a knife that is movable between the linear rows of surgical fasteners such that the tissue being joined and/or sealed is simultaneously, or nearly simultaneously, cut upon actuation of the surgical fastener applying apparatus. Given this capability, surgical fastener applying apparatus of the linear variety are commonly used during surgical procedures to simultaneously seal and cut tissue, e.g., a patient's vasculature, organs, or the like.

It is not uncommon that certain tissue portions, e.g., vasculature or other connective tissues, adhere to, or are naturally joined with, other tissue portions. Accordingly, a surgical fastener applying apparatus including structure capable of separating the first tissue portion from these adherent second tissue portions would be desirable to facilitate isolation of the first tissue portion before continuing with the surgical procedure.

SUMMARY

Introducer assemblies in accordance with the present disclosure can be releasably coupled to a surgical instrument, such as for example, to a minimally invasive surgical stapler. The introducer assembly includes a collar configured to releasably couple to a portion of a surgical instrument, a tip configured to mount to the distalmost end of the surgical instrument, and a body portion connecting the collar to the tip.

In one aspect of the present disclosure, an introducer assembly in accordance with the present disclosure is releasably coupled to a surgical fastener applying apparatus. The surgical fastener applying apparatus includes an elongated shaft, an end effector positioned at a distal portion of the elongated shaft, and an introducer assembly releasably coupled to the end effector. The end effector includes a first jaw movably coupled to a second jaw such that tissue is positionable therebetween. The introducer assembly includes a collar, a tip, and an elongated body portion between the collar and the tip. The introducer assembly is releasably attached to the end effector. The proximal portion of the tip may be elastomeric and may include an opening that conforms to a shape and size of the jaw when the tip is attached to the jaw. In embodiments, the tip includes an attachment structure for releasably engaging an interchangeable dissecting device. In embodiments, the attachment structure is a second opening located at a distal portion of the tip.

In one aspect, the introducer assembly is secured to the end effector such that the collar is releasably or slidably attached to a proximal portion of the end effector and the tip is releasably or slidably attached to a distal portion of either the first jaw or second jaw. In embodiments, a portion of the tip of the introducer assembly may be coated with an epoxy to modify the surface properties of the tip, thereby facilitating passage of the tip between tissue portions. Additionally, in embodiments, the introducer assembly may be coated, entirely or partially, with an epoxy. In embodiments, the collar, the tip, and the body portion are monolithically formed.

In embodiments, the collar is substantially cylindrical in shape. An inner diameter of the collar may be uniform. Alternatively, an inner surface of the collar may be tapered (cone shaped) such that an inner diameter of a proximal portion of the collar is larger than an inner diameter of a distal portion of the collar.

In another aspect of the present disclosure, a dissecting kit includes an introducer assembly and at least one interchangeable dissecting device releasably attachable to a distal portion of the introducer assembly.

In another aspect of the present disclosure, a dissecting kit includes a first introducer assembly and a second introducer assembly. The first introducer assembly has a first collar and a first tip. The second introducer assembly has a second collar and a second tip. The second tip may be different from the first tip in at least one configuration. In embodiments, the dissecting kit includes a third introducer assembly having a third collar and a third tip. The third tip may be different from the first and second tips and may further be configured to releasably receive a dissecting device.

These and other features of the presently disclosed introducer assembly will become more readily apparent to those skilled in the art through reference to the detailed description of various aspects of the present disclosure that follows.

BRIEF DESCRIPTION OF THE DRAWINGS

Various aspects of the present disclosure are described herein below with references to the drawings, wherein:

FIG. 1A is a perspective view of a surgical fastener applying apparatus including an introducer assembly removably coupled to an anvil assembly in accordance with one aspect of the present disclosure;

FIG. 3A is a bottom view of the introducer assembly of FIGS. 1A-1B;

FIG. 3B is a side view of the introducer assembly of FIGS. 1A-1B;

FIG. 4A is a side, perspective view of a distal portion of the surgical fastener applying apparatus of FIGS. 1A-1B illustrating the presently disclosed introducer assembly prior to attachment to the end effector;

FIG. 4B is an enlarged view of the area of detail in FIG. 1A;

DETAILED DESCRIPTION OF THE EMBODIMENTS

Figure 1B:
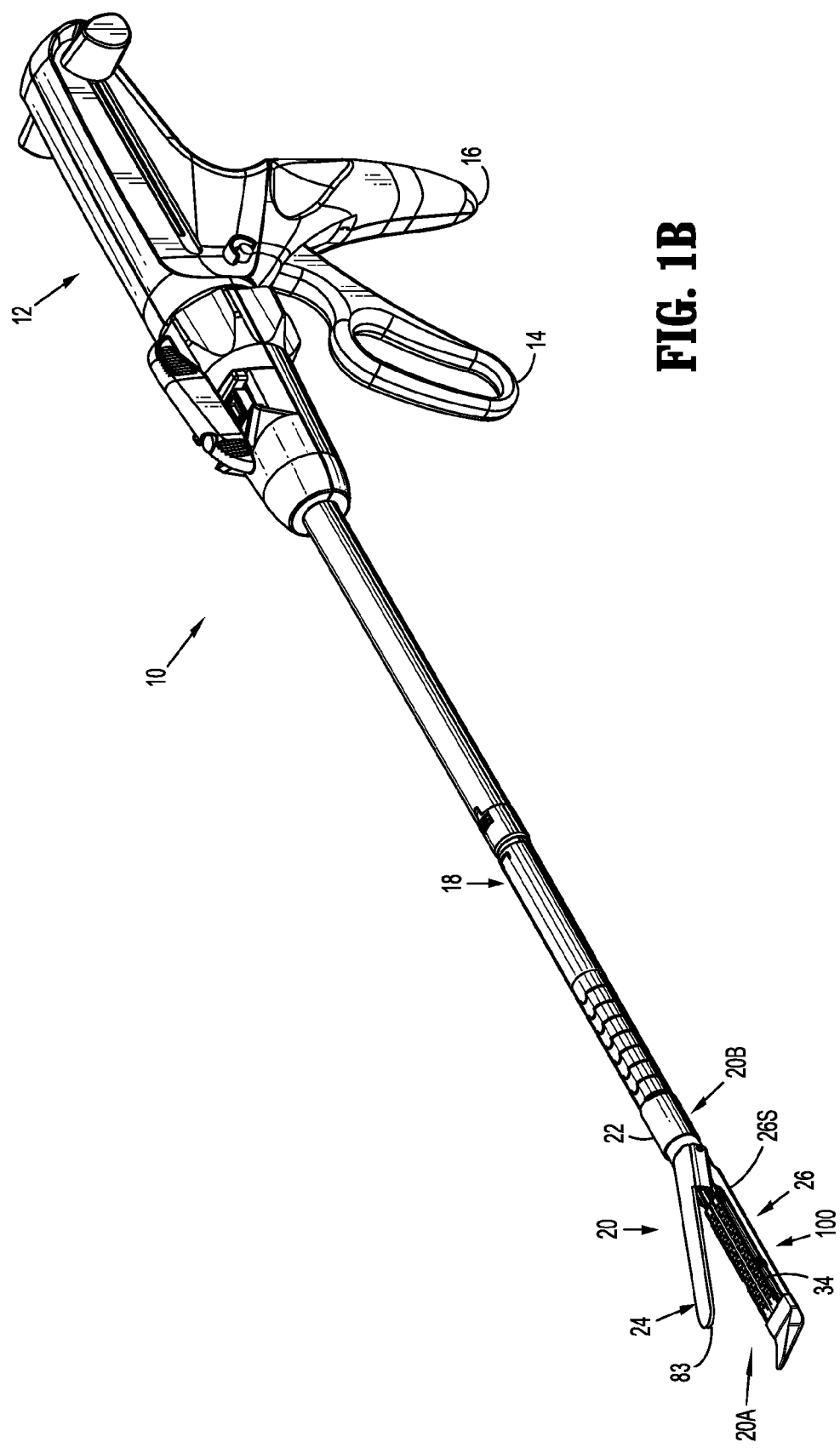
FIG. 1B is a perspective view of a surgical fastener applying apparatus including an introducer assembly removably coupled to a cartridge assembly in accordance with one aspect of the present disclosure.
Figure 2A:
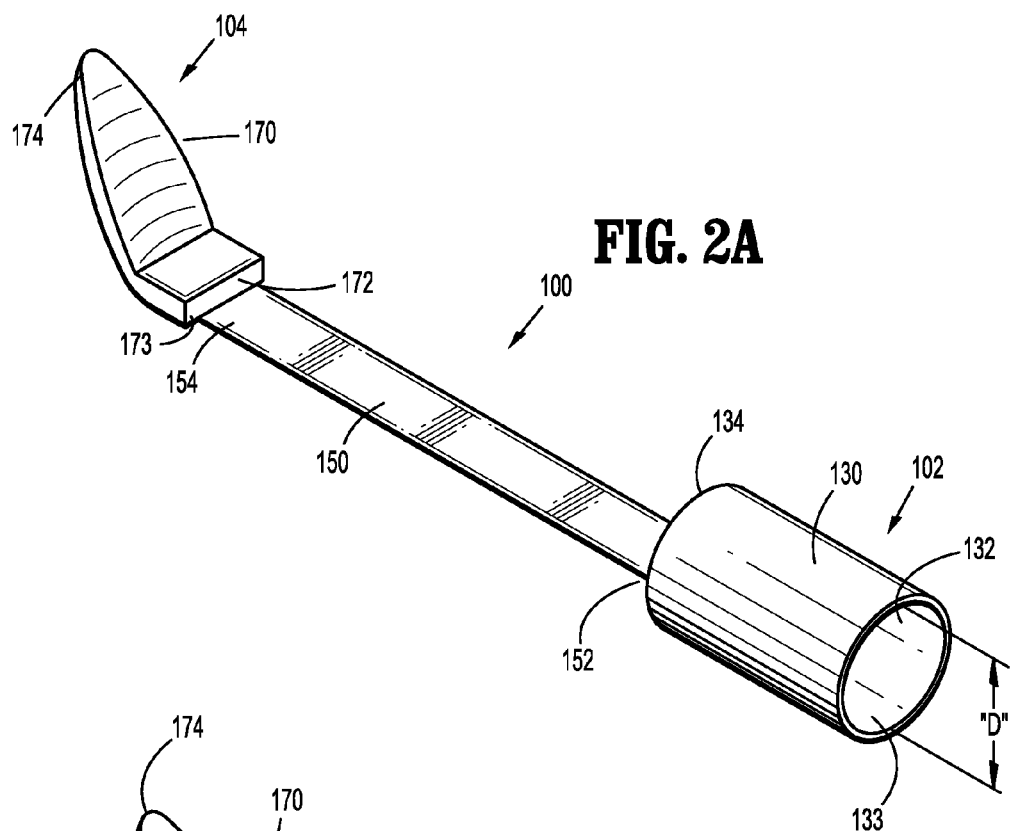
FIG. 2A is a side, perspective view of the introducer assembly of FIGS. 1A-1B.
Figure 2B:
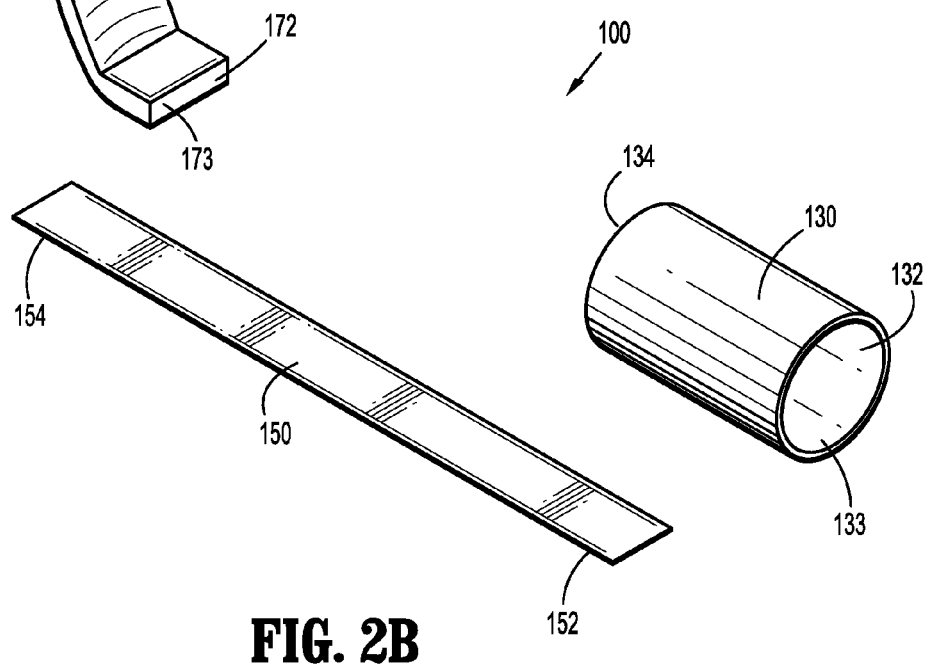
FIG. 2B is a side, perspective view of the introducer assembly of FIGS. 1A-1B, with parts separated.
Figure 5A:
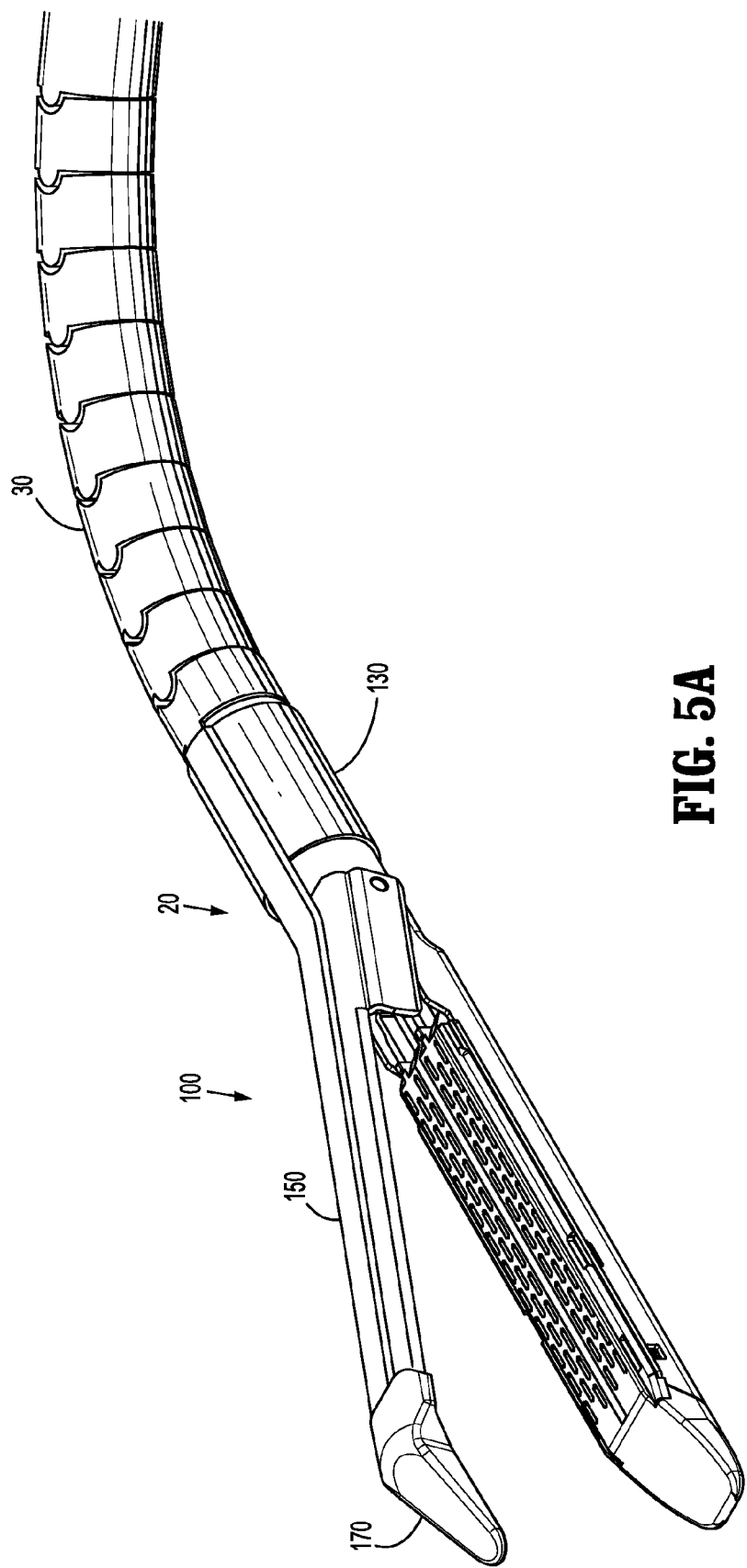
FIG. 5A is a top perspective view of a distal portion of the surgical fastener applying apparatus of FIGS. 1A-1B illustrating the presently disclosed introducer assembly after attachment to the end effector.
Figure 5B:
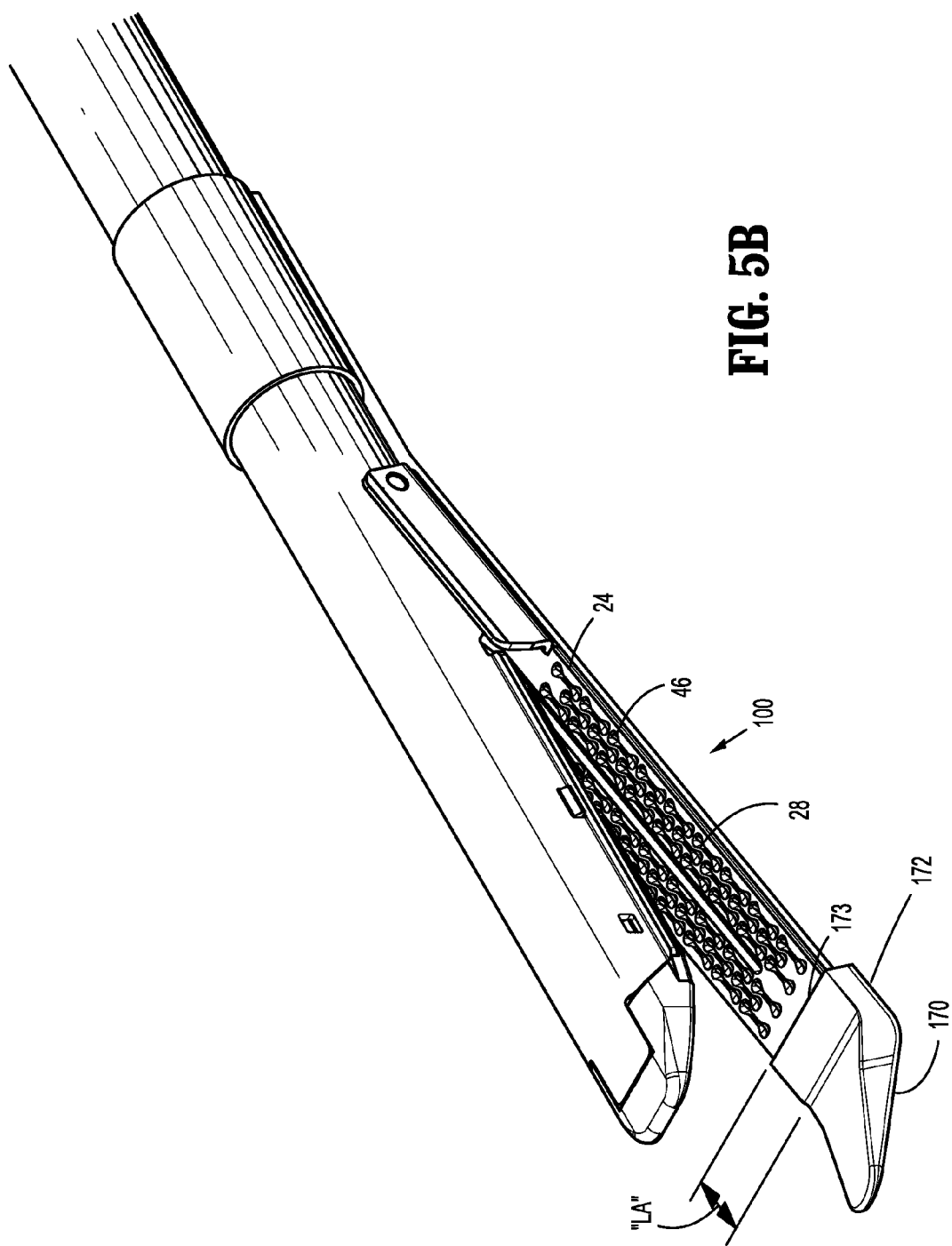
FIG. 5B is a bottom perspective view of a distal portion of the surgical fastener applying apparatus of FIGS. 1A-1B illustrating the presently disclosed introducer assembly after attachment to the end effector.

Various aspects of the presently disclosed surgical fastener applying apparatus, introducer assembly, interchangeable dissecting device, and methods of using the same will now be described in detail with reference to the drawings wherein like references numerals identify similar or identical elements. In the drawings, and in the following description, the term "proximal" should be understood as referring to the end or portion of the surgical fastener applying apparatus, introducer assembly, or interchangeable dissecting device discussed below, or component thereof, that is closer to the clinician during proper use, while the term "distal" should be understood as referring to the end or portion that is farther from the clinician, as is traditional and conventional in the art. In addition, the term "surgical fastener" should be understood to include any structure formed of a biocompatible material that is suitable for the purpose of joining tissue together, including but not being limited to surgical staples, clips, and the like. Moreover, the term "tissue" should be understood as referring to any human or animal tissue, artery, vein, organ, or other such anatomical structure found within the body.

FIGS. 1A-1B illustrate a surgical fastener applying apparatus 10, of either the re-usable or disposable variety, that includes a handle assembly 12 with a movable handle 14 and a stationary handle 16, an elongated shaft 18 that extends distally from the handle assembly 12, an end effector 20 that is positioned at a distal portion 22 of the elongated shaft 18, and an introducer assembly 100 that is releasably connectable to the end effector 20 or the distal portion 22 of the elongated shaft 18.

In various aspects, it is envisioned that the handle assembly 12 may include motor-driven, hydraulic, ratcheting, or other such mechanisms to facilitate actuation of the surgical fastener applying apparatus 10.

In general, the end effector 20 is adapted to clamp, fasten together, and sever adjacent tissue segments along a cut-line. During use, the jaws 24, 26 of the surgical fastener applying apparatus 10 are approximated and fired similarly to, and in accordance with, other known surgical fastener applying apparatus. Additional details regarding approximation and firing of surgical fastener applying apparatus 10 may be obtained through reference to commonly owned U.S. Pat. No. 5,865,361, the entire contents of which are hereby incorporated by reference.

Continuing with reference to FIGS. 1A-1B, the end effector 20 includes a first jaw 24 that is pivotally coupled to a second jaw 26 to facilitate approximation thereof, and is adapted to clamp, fasten together, and sever adjacent tissue segments along a cut-line. The first jaw 24 of the end effector 20 includes an anvil member 28, and the second jaw 26 includes a surgical fastener cartridge 34 that is loaded with a plurality of surgical fasteners. Pivoting the movable handle 14 towards the stationary handle 16 approximates the first jaw 24 and the second jaw 26.

FIG. 1A illustrates a surgical fastener applying apparatus 10 having an introducer assembly 100 removably coupled to the first jaw 24 (or anvil member 28) of the end effector 20. FIG. 1B illustrates a surgical fastener applying apparatus 10 having an introducer assembly 100 removably coupled to the second jaw 26 (or the surgical fastener cartridge 34) of the end effector 20. Thus, the introducer assembly 100 may accommodate different end effectors 20 of different surgical fastener applying apparatus 10, and either one of the jaws 24, 26 of the end effectors 20.

With reference now to FIGS. 1A-1B, 2A-2B, and 3A-3B, one aspect of the presently disclosed introducer assembly, which is identified by the reference character 100, will be described. The introducer assembly 100 includes proximal portion 102 and distal portion 104 (FIG. 2A), and may be formed from a pliable, biocompatible material, including but not limited to polymeric materials, such as rubbers or plastics. In one particular aspect, it is envisioned that the introducer assembly 100 may be entirely formed from a flexible and/or elastomeric material. Alternatively, however, it is envisioned that the introducer assembly 100 may be formed at least in part of rigid materials. Alternatively, the introducer assembly 100 may include portions of increased rigidity formed from a higher durometer material to provide additional structure to portions of the introducer assembly 100, and/or assist in the separation of tissue.

The introducer assembly 100 is configured, dimensioned, and adapted to guide the end effector 20 into position between tissue portions. In one aspect, a portion of tissue may be the subject of the surgical procedure. In other aspects, a portion of the tissue may be tissue that a surgeon desires to move or manipulate. To this end, the tip 170 of the introducer assembly 100 may include a partially or wholly curved configuration that defines an arc substantially in the range of approximately 5° to approximately 90°. In one aspect, for example, the tip 170 of the introducer assembly 100 curves from the anvil member 28 towards the surgical fastener cartridge 34, and is oriented such that the tip 170 extends beyond the distal portion 20A of the end effector 20, so that tissue may be approached at an angle and directed between the jaws 24, 26 of the surgical fastener applying apparatus 10. It should be appreciated, however, that the tip 170 of the introducer assembly 100 may curve in any direction suitable for the intended purpose of guiding the instrument into position and/or facilitating separation of the tissue portions. Additionally, it should be appreciated that the tip 170, and/or any interchangeable dissecting devices 181 (FIG. 7A) may be malleable or bendable such that a clinician may alter the curve as desired.

The introducer assembly 100 may have any cross-sectional configuration suitable for atraumatically separating tissue portions. For example, the introducer assembly 100 may have an oval cross-sectional configuration, a substantially rounded cross-sectional configuration, or a polygonal cross-sectional configuration, as will be described in further detail below.

With the introducer assembly 100 connected to the end effector 20 (e.g., the introducer assembly 100 is positioned about any one of the anvil member 28, first jaw 24, second jaw 26, or the surgical fastener cartridge 34) (FIGS. 1A-1B), the assembly of the surgical fastener applying apparatus 10 (FIGS. 1A-1B) and the introducer assembly 100 can be manipulated. In one aspect, the end effector 20 may be articulatable, thereby allowing the clinician to selectively reconfigure the introducer assembly 100, and effectively steer the introducer assembly 100 between tissue portions when the introducer assembly 100 is coupled to the end effector 20.

Referring now to FIGS. 2A-2B and 3A-3B, introducer assembly 100 will be discussed with particular detail. Introducer assembly 100 includes a collar 130, an elongated central body portion 150, and a tip 170. Collar 130 is disposed on a proximal portion 102 of introducer assembly 100 and tip 170 is disposed on a distal portion 104 of introducer assembly 100. In aspects, each of collar 130, body portion 150, and tip 170 are separate components that are attachable to each other to form introducer assembly 100. Alternatively, in aspects, collar 130, body portion 150, and tip 170 are monolithically formed or preassembled to form introducer assembly 100.

Collar 130 defines a hollow opening 133 therethrough configured and dimensioned to slidably engage end effector 20 or distal portion 22 of elongated shaft 18 of surgical fastener applying apparatus 10 (FIG. 4B). Hollow opening 133 includes an inner diameter "D" (FIG. 2A), which may be substantially uniform throughout the entire hollow opening 133 or may alternatively vary along the length of hollow opening 133. In this regard, collar 130 includes a proximal portion 132 configured to slide over the end effector 20, as will be discussed in further detail below with reference to FIGS. 4A-4B. Collar 130 may be formed of a substantially rigid material, or alternatively may be formed of a substantially flexible and/or elastomeric material. When collar 130 is formed of a flexible and/or elastomeric material, the shape and size of collar 130 may conform to the shape and size of the end effector 20 when collar 130 is positioned on the end effector 20. Collar 130 and additional aspects of collar 130 will be discussed in further detail below with reference to FIGS. 6A-6B.

Elongated central body portion 150 is coupled to the collar 130. In aspects, body portion 150 is substantially planar, such that it may abut the top surface 24$s$ (FIG. 1A) of first jaw 24 or a bottom surface 26$s$ (FIG. 1B) of second jaw 26 in a low profile manner. In aspects, body portion 150 includes gripping elements (not shown) on its inner jaw contacting surface to effect a better placement and grip on first jaw 24 or second jaw 26. As seen best in FIG. 3A, body portion 150 includes length "L." In aspects, length "L" is substantially similar to the length of the first jaw 24 or anvil member 28. Body portion 150 may be coupled to any region of collar 130. For example, as seen in FIG. 3B, proximal portion 152 of body portion 150 is coupled to the entire collar 130 from the proximal portion 132 of collar 130 to the distal portion 134 of collar 130. Thus, length "L" may vary depending on the orientation of body portion 150 to collar 130.

As described above, the introducer assembly 100 includes a tip 170 disposed at a distal portion 104 of introducer assembly 100. Proximal portion 172 of tip 170 defines, or otherwise includes, an opening 173 dimensioned to facilitate engagement with a distal portion 20A (FIGS. 4A-4B) of end effector 20. More particularly, opening 173 is dimensioned to facilitate engagement with first jaw 24 or anvil member 28 of surgical fastener applying apparatus 10 (FIG. 1A) or second jaw 26 or cartridge assembly 34 of surgical fastener applying apparatus 10 (FIG. 1B). In aspects, proximal portion 172 of tip 170 is substantially expandable such that opening 173 may stretch, or otherwise conform, to the shape of different jaw members, anvils, or cartridges of different sizes and shapes.

As seen best in FIG. 4B, when the distal portion 24A of the first jaw 24 is inserted into the opening 173, the proximal portion 172 of the tip 170 will not obstruct or interfere with any of the forming surfaces of the pockets (not shown) of the anvil member 28. Tip 170 may be coupled, and/or secured, to the first jaw 24 or anvil member 28 using any known fastening technique. In one aspect, tip 170 is coupled to the first jaw 24 or anvil member 28 via a friction fit. In aspects, tip 170 is formed from surgical grade metals or plastics although other known materials of construction are envisioned.

In an aspect, tip 170 includes an elongate profile that tapers towards the distal portion 174 of tip 170. Including a tapered profile on the tip 170 allows the distal portion 104 of the introducer assembly 100 to define a reduced cross-sectional area when compared to more proximal portions thereof in order to facilitate advancement of the introducer assembly 100, in particular the tip 170, through the patient's tissue. Additionally, the reduced cross-sectional area at the distal portion 174 of the tip 170 facilitates access to internal spaces and tissues that would otherwise be inaccessible given the larger dimensions of the end effector 20 (FIGS. 1A-1B), and reduces trauma upon the patient's internal tissues. For example, in one aspect, it is envisioned that the distal portion 174 of the tip 170 may have a transverse dimension in the range of approximately 2 mm to approximately 6 mm, although dimensions that are both larger and smaller are within the scope of the present disclosure.

Additionally, to facilitate distal advancement and navigation of the introducer assembly 100 between tissue portions, it is envisioned that the introducer assembly 100 may include a dual taper. Specifically, the tip 170 of introducer assembly 100 may include a tapered profile that decreases in cross-sectional height and width from the proximal portion 172 of tip 170 to the distal portion 174 of tip 170.

In aspects, tip 170 is partially, or entirely, coated by an epoxy material and/or resin. Coating tip 170 with an epoxy provides a smoother surface which may assists in tissue dissection or separation. Additionally, the epoxy coating may provide a more tapered and less bulbous shape between the distal portion 174 and proximal portion 172 of tip 170. Additionally, epoxy material may be provided on any of the other components of the introducer assembly 100 in addition to the tip 170, such as the collar 130 and/or the body portion 150.

Introducer assembly 100 may be monolithically formed. In one aspect, introducer assembly 100 is manufactured using welded interlocking metal tubing.

To facilitate engagement with, and disengagement from, the end effector 20 (FIGS. 1A-1B), it is envisioned that the introducer assembly 100 may incorporate an adhesive, or alternatively, that the introducer assembly 100 may include structure that is configured and dimensioned for engagement with corresponding structure formed on the end effector 20. As described above, in one aspect, introducer assembly 100 is coupled to end effector 20 via a friction fit engagement.

Referring now to FIGS. 4A-4B and 5A-5B, attachment of the introducer assembly 100 to the surgical fastener applying apparatus 10 will now be described. FIG. 4A illustrates the introducer assembly 100 prior to attachment to the end effector 20 and FIG. 4B illustrates the introducer assembly 100 subsequent to being attached to the end effector 20. Although described as being attached to the end effector 20, it is envisioned that portions of the introducer assembly 100 (i.e., the collar 130) may be coupled to any portion of the surgical fastener applying apparatus 10, such as the distal portion 22 of the elongated shaft 18, and/or a combination of the elongated shaft 18 and the end effector 20.

To secure the introducer assembly 100 to the end effector 20, a user slides the introducer assembly 100 over the end effector 20. In particular, while the first jaw 24 and the second jaw 26 are in the closed position, a user may slide the introducer assembly 100 in the direction of arrow "A" over the first jaw 24 and the second jaw 26. Proximal portion 20B of end effector 20 includes an outer diameter "d" which is slightly smaller than the inner diameter "D" of collar 130. However, in some aspects, outer diameter "d" of end effector 20 may be equal to, or greater than, the inner diameter "D" of collar 130. In this regard, and as described above, collar 130 may be formed of a flexible and/or elastomeric material such that the inner diameter "D" of collar 130 expands when placed over the proximal portion 20B of end effector 20. In certain aspects, a surgical fastener applying apparatus 10 may be preassembled with the introducer assembly 100, as shown in FIG. 4B.

Continuing with reference to FIGS. 4A-4B, in some aspects, distal portion 22 of elongated shaft 18, and/or proximal portion 20B of end effector 20, may include an articulation assembly 30. In order to not obstruct or interfere with the movement of articulation assembly 30 during use, collar 130 may be advanced over the closed first and second jaw 24, 26 to a portion of the end effector 20 that is distal to the articulation assembly 30 as shown in FIG. 4B. However, in embodiments where collar 130 is formed of a flexible and/or elastomeric material, introducer assembly 100 may be advanced such that collar 130 is positioned over articulation assembly 30. In this regard, where collar 130 is flexible and/or elastomeric, collar 130 will articulate with the movement of the articulation assembly 30, and thus will not obstruct movement of the articulation assembly 30.

Introducer assembly 100 is advanced in the direction of arrow "A" until the distal portion 104 of introducer assembly 100 reaches the distal portion 20A of the end effector 20, in particular the distal portion 24A of the first jaw 24. As distal portion 104 of introducer assembly 100 is advanced toward distal portion 24A of first jaw 24, distal portion 24A of first jaw 24 is inserted into opening 173 of tip 170 and secured there. As described above, proximal portion 172 of tip 170 may be formed of a substantially flexible and/or elastomeric material, such that opening 173 may frictionally engage the distal portion 24A of first jaw 24 when distal portion 24A of first jaw 24 is inserted into opening 173 of the tip 170.

As seen best in FIG. 4B, once introducer assembly 100 is attached to end effector 20, first jaw 24 and second jaw 26 are free to move between open and closed positions. In this regard, body portion 150 may be flexible and/or elastomeric such that body portion 150 may bend or flex during movement of jaws 24, 26 between the open and closed positions. In addition to the other methods described above, a user may move the introducer assembly 100 by articulating the end effector 20 via articulating assembly 30, by moving the entire surgical fastener applying apparatus 10, by moving the first jaw 24 via handle assembly 12.

Although described above as being connected to the first jaw 24 or anvil member 28, it is appreciated that introducer assembly 100, in particular tip 170, may be releasably coupled to the second jaw 26 or fastener cartridge 34 in the same manner as described with respect to FIGS. 4A-4B.

Application of surgical fasteners to tissue is unaffected even while the introducer assembly 100 is attached to the end effector 20. Specifically, surgical fasteners may be ejected from fastener cartridge 34 without ever coming into contact with any part of introducer assembly 100. Thus, the introducer assembly 100 does not obstruct engagement of the surgical fasteners with the pockets of the anvil member 28 or interfere with any ejection of the surgical fasteners. Similarly, when introducer assembly 100 is coupled to the second jaw 26 or the cartridge assembly 34 (FIG. 1B), passage of the surgical fasteners through the cartridge assembly 34 is also unobstructed.

Figure 6A:
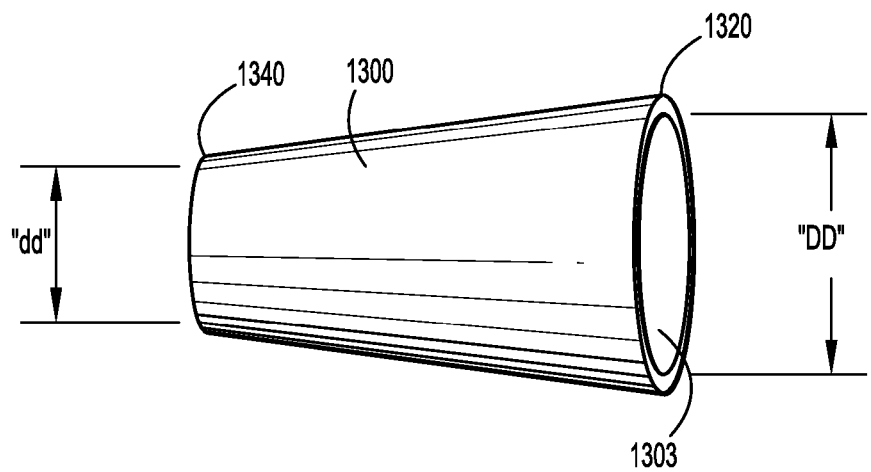
FIG. 6A is a side, plan view illustrating another aspect of a collar for use with an aspect of introducer assembly.
Figure 6B:
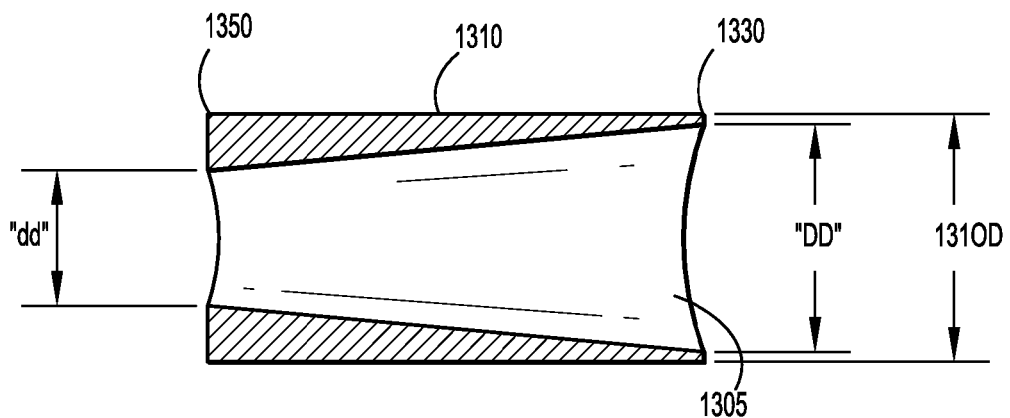
FIG. 6B is a side, cross-sectional view of yet another aspect of a collar that may be implemented with another aspect of introducer assembly.

FIGS. 6A-6B illustrate other aspects of the presently disclosed collar 130 that may be used with introducer assembly 100, illustrated and described as collar 1300 and collar 1310, each of which will be described in further detail below.

With particular reference to FIG. 6A, collar 1300 is illustrated having a tapered outer shape with a substantially similar inner taper. Collar 1300 is similar to collar 130 and therefore only the differences between the two will be described. Proximal portion 1320 of collar 1300 includes an inner diameter "DD" and distal portion 1340 of collar 1300 includes an inner diameter "dd" which is smaller than inner diameter "DD," thus defining a substantially tapered inner hollow opening 1303. In this regard, both the outer and inner diameters of collar 1300 vary between the proximal portion 1320 and the distal portion 1340 to form the generally tapered shape. Collar 1300 may be used on different surgical devices that have different size end effectors 20 or different size distal portions 22 of elongated shafts 18. In this regard, when collar 1300 is advanced onto an end effector 20, collar 1300 will continue to advance until the collar 1300 is securely fitted to the end effector 20. Collar 1300 will be securely fitted to end effector 20 at a point where the outer diameter "d" of end effector 20 is substantially similar to the inner diameter of collar 1300, e.g., at some point between proximal portion 1320 and distal portion 1340 of collar 1300.

Referring now to FIG. 6B, another aspect of collar 130 is shown and described as collar 1310. Collar 1310 is similar to collars 130 and 1300 and therefore only the differences between the two will be described. Collar 1310 includes a substantially uniform outer shape with a substantially tapered hollow opening 1305. Collar 1310 includes a proximal portion with an inner diameter "DD" and a distal portion 1350 with an inner diameter "dd" which is smaller than the inner diameter "DD." However, unlike collar 1300, collar 1310 includes a substantially uniform outer diameter 1310D between the proximal portion 1330 and the distal portion 1350. In this regard, similar to collar 1300, collar 1310 may be used with different surgical devices having different size end effectors 20 and distal portions 22 of elongated shafts 18, but the outer diameter 1310D is substantially uniform.

Turning now to FIGS. 7A-7D and 8, additional aspects of introducer assembly 100 are illustrated and will be described as introducer assembly 100b, introducer assembly 100c, introducer assembly 100d, and introducer assembly 100e, respectively.

Figure 7A:
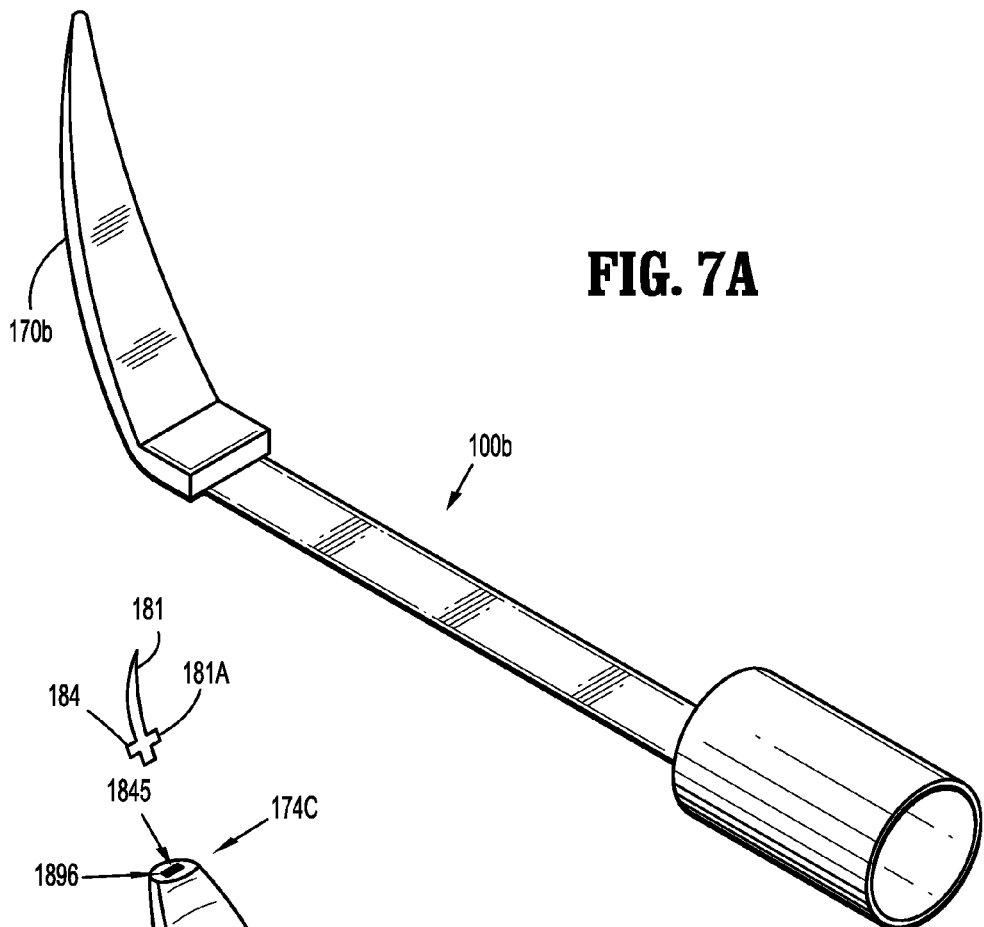
FIG. 7A is a perspective view of another aspect of introducer assembly.
Figure 10A:
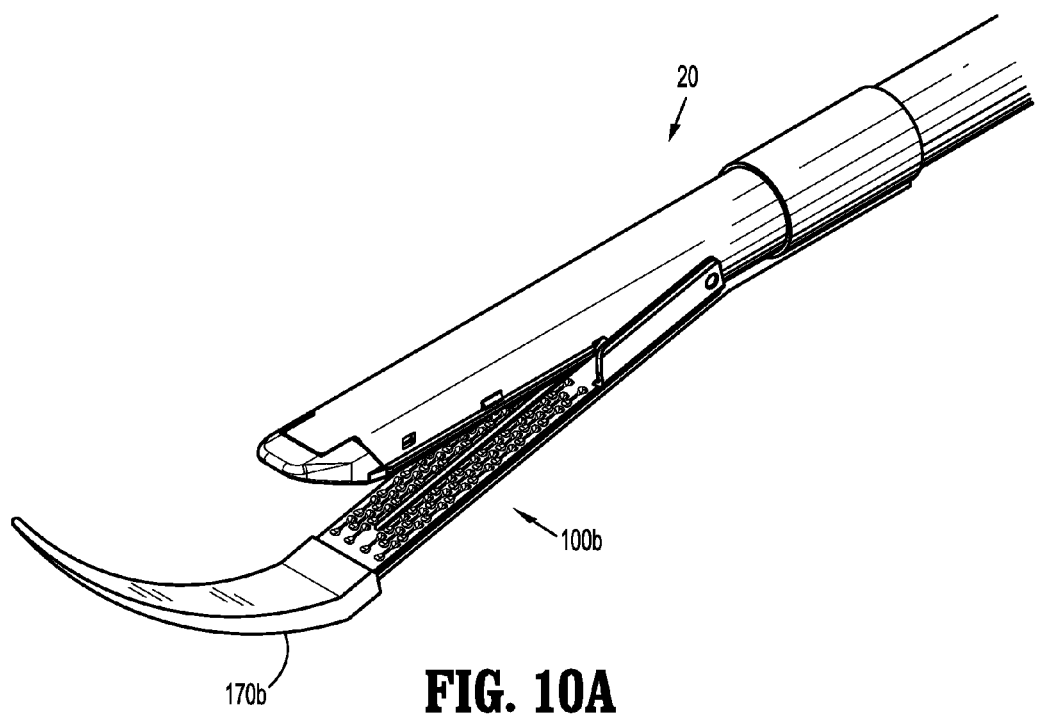
FIG. 10A is a top perspective view of a distal portion of the surgical fastener applying apparatus of FIGS. 1A-1B illustrating an embodiment of a presently disclosed introducer assembly after attachment to the end effector.

With particular reference to FIG. 7A, introducer assembly 100b having tip 170b is illustrated. Introducer assembly 100b is similar to introducer assembly 100 and therefore only the differences between the two will be described. Tip 170b has a different size, shape, and/or configuration than tip 170. In particular, tip 170b is elongated to assist in dissecting portions of tissue. Tip 170b may be substantially rigid or alternatively may be malleable such that a user may manipulate the shape of tip 170b. With brief reference to FIG. 10A, introducer assembly 100b is illustrated after being attached to an end effector 20.

Figure 7B:
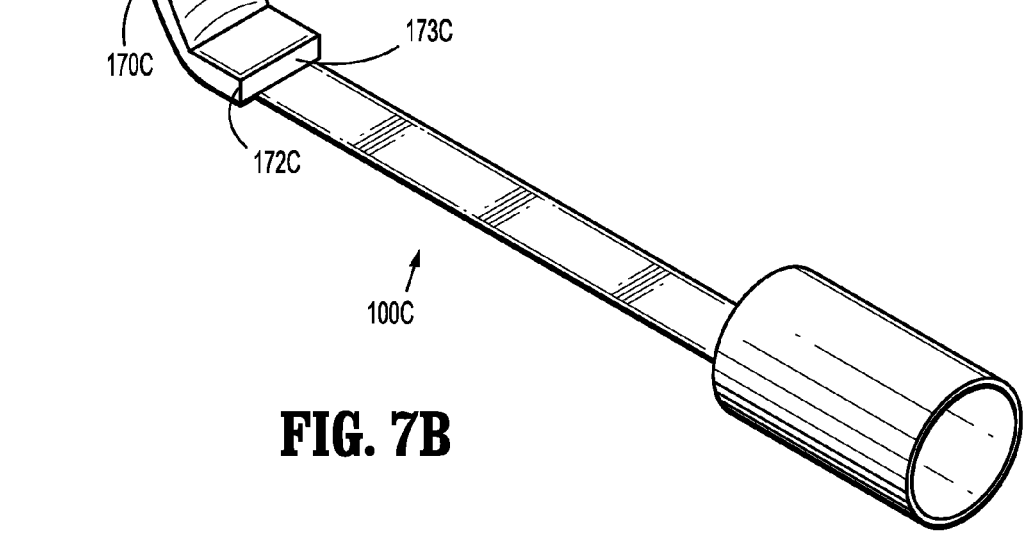
FIG. 7B is a perspective view of yet another aspect of introducer assembly.

With particular reference to FIG. 7B, introducer assembly 100c having tip 170c is illustrated and will be described. Introducer assembly 100c is similar to introducer assembly 100 and therefore only the differences between the two will be described. In addition to opening 173c disposed at the proximal portion 172c of tip 170c, tip 170c further includes an attachment structure, such as a second opening 1845, disposed at the distal portion 174c of tip 170c. Second opening 1845 is configured and dimensioned to facilitate attachment to an interchangeable dissecting device 181. Interchangeable dissecting device 181 may be attached to tip 170c in any suitable manner. Interchangeable dissecting device 181 may be any suitable dissecting device. It is envisioned that several different types of interchangeable dissecting devices 181, with different configurations, may be used in conjunction with tip 170c.

Interchangeable dissecting devices 181 may assume a variety of configurations in any or all of shape, size, or composition. For example, interchangeable dissecting device 181 may include an elongate configuration. Additionally, in aspects, interchangeable dissecting device 181 may include an illuminating portion. Additionally, interchangeable dissecting device 181 may be substantially transparent. In this regard, a light emitting device may be included in surgical fastener applying apparatus 10 and/or introducer assembly 100c such that light may pass through introducer assembly 100c and interchangeable dissecting device 181 to increase visibility of a surgical area. Additionally, in aspects, interchangeable dissecting device 181 may be substantially malleable, such that a user may manipulate the shape and configuration of the interchangeable dissecting device 181 to suit the needs of the particular dissection of tissue being performed.

Continuing with reference to FIG. 7B, it is envisioned that the proximal portion 181A of the interchangeable dissecting device 181 and the second opening 1845 of the tip 170c may include corresponding structure that is configured and dimensioned for mating engagement. For example, the proximal portion 181A of the interchangeable dissecting device 181 may include an attachment structure 184 configured and dimensioned for connection with corresponding engagement structure 1896 formed within the second opening 1845 at the distal 174c of the tip 170c in a press-fit arrangement. In the illustrated embodiment, the attachment structure 184 is depicted as including a plurality of protrusions, and the engagement structure 1896 is depicted as including recesses of corresponding configuration and dimensions. It should be appreciated, however, that alternative configurations for the attachment structure 184 and the engagement structure 1896 are not beyond the scope of the present disclosure.

Figure 10B:
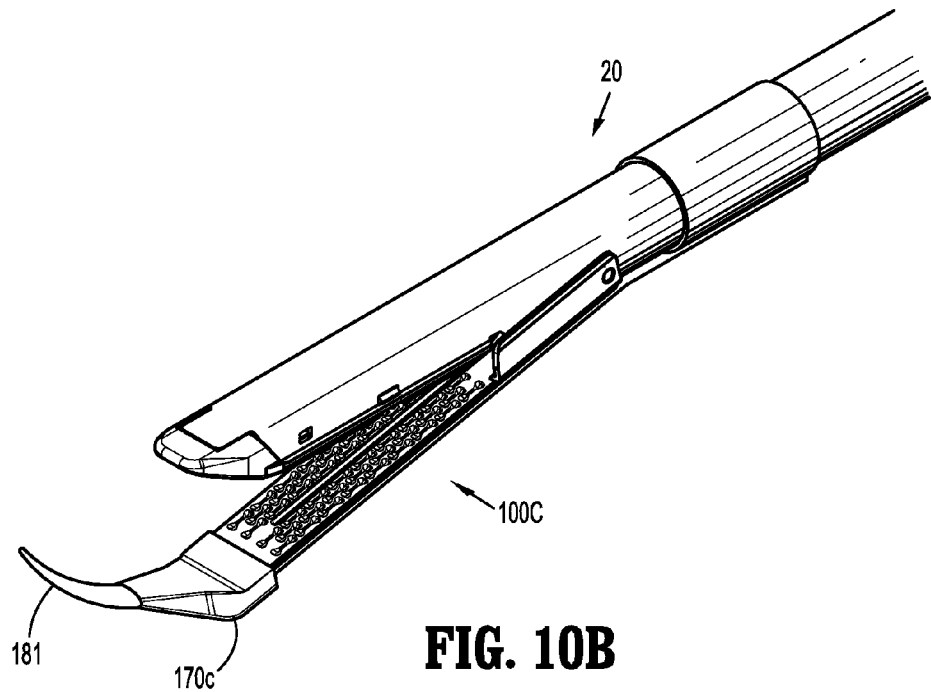
FIG. 10B is a top perspective view of a distal portion of the surgical fastener applying apparatus of FIGS. 1A-1B illustrating another embodiment of a presently disclosed introducer assembly after attachment to the end effector.

To facilitate advancement of, and control over, the introducer assembly 100c during manipulation within an internal workspace, it is envisioned that the tip 170c may be formed from a first material, e.g., a rigid material, such as solid or sheet metal, and that the interchangeable dissecting device 181 may be formed from a second, more flexible and/or elastomeric material, such as plastic or rubber. With brief reference to FIG. 10B, introducer assembly 100c is illustrated after being attached to an end effector 20.

Figure 7C:
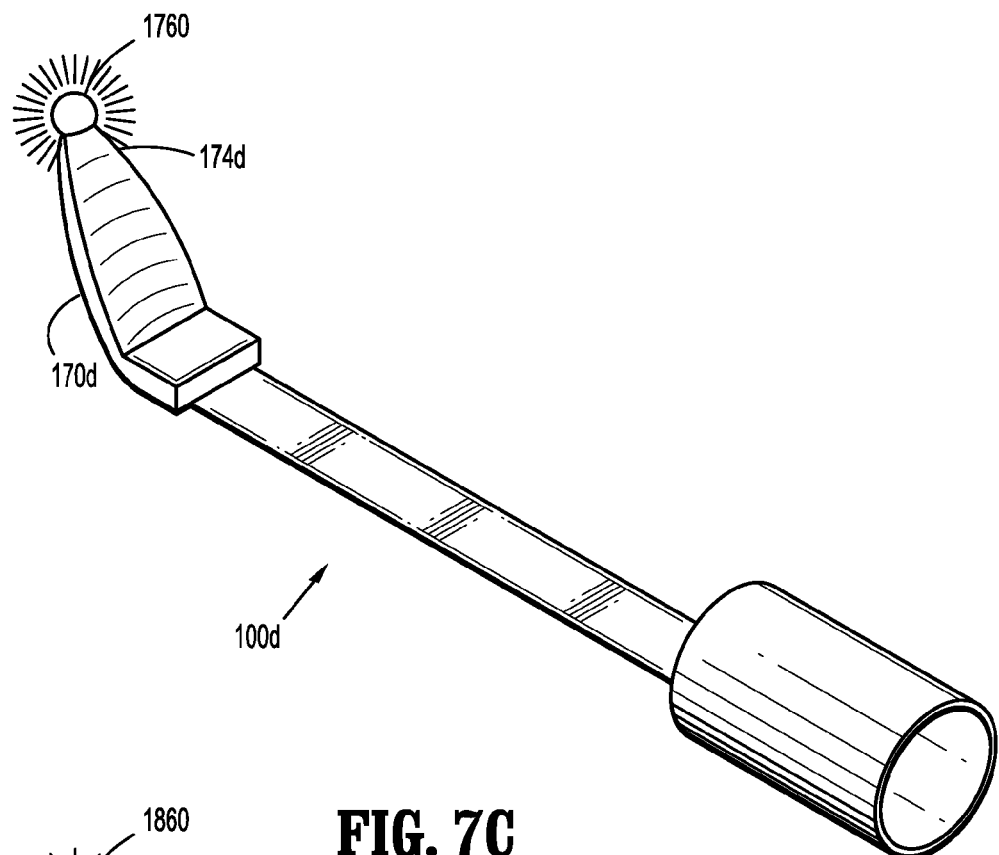
FIG. 7C is a perspective view of yet another aspect of introducer assembly.

With particular reference to FIG. 7C, introducer assembly 100d having tip 170d is illustrated and will be described. Introducer assembly 100d is similar to introducer assembly 100 and therefore only the differences between the two will be described. Tip 170d includes an illuminating element 1760 on the distal portion 174d of tip 170d. In embodiments, illuminating element 1760 is a fluorescent element capable of emitting light without a power source. In alternative embodiments, illuminating element 1760 is an assembly including a power source, such as a battery or any other suitable power source, and a light source, such as a laser, light emitting diode, or any other such light emitting device capable of producing or transferring light to the surgical site to increase visibility of the surgical site for the user.

Figure 7D:
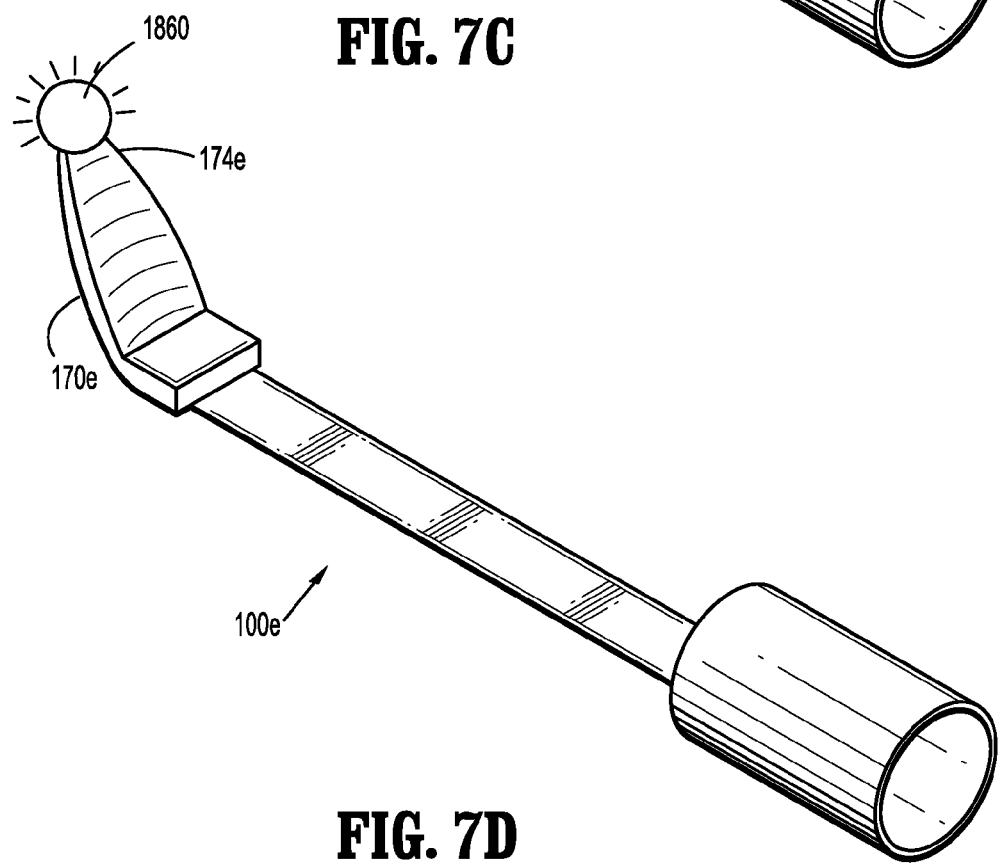
FIG. 7D is a perspective view of yet another aspect of introducer assembly.

With particular reference to FIG. 7D, introducer assembly 100e having tip 170e is illustrated and will be described. Introducer assembly 100e is similar to introducer assembly 100 and therefore only the differences between the two will be described. Tip 170e includes an imaging device 1860 on the distal portion 174e of tip 170e. Imaging device 1860 may be an assembly that includes an image capturing element and a power source. During use, a surgeon or clinician may have another imaging device, such as a laparoscope, inserted into the surgical site, and imaging device 1860 may be used to provide an important alternative, or different perspective, view of the surgical site. In particular, although a laparoscope may provide a surgeon with a general view of the surgical site, with an imaging device 1860 disposed on a distal end 174e of tip 170e, the surgeon is provided with a better view of the tissue being dissected (i.e., the tissue in contact with the tip 170e).

Figure 8:
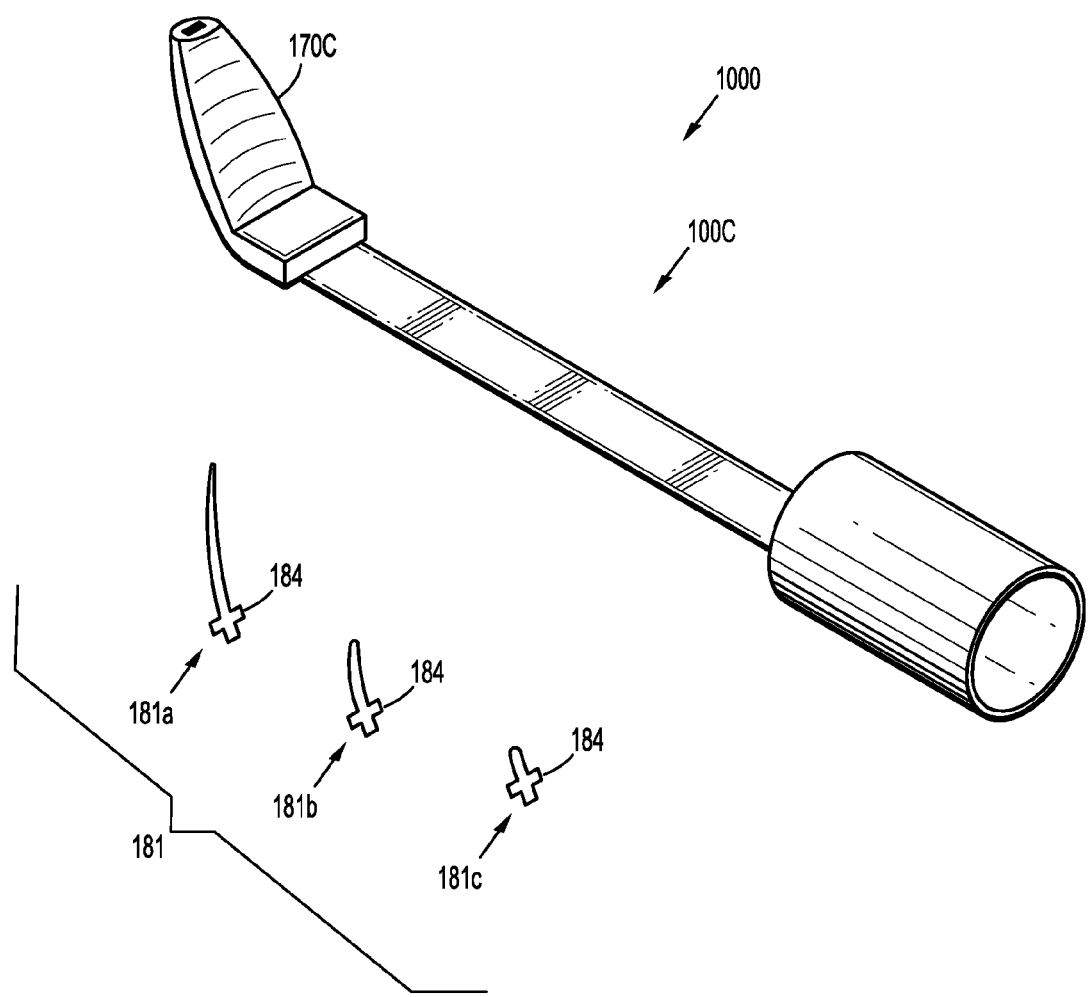
FIG. 8 is a perspective view illustrating a kit including an introducer assembly and interchangeable dissecting devices in accordance with an aspect of the present disclosure.
Figure 9:
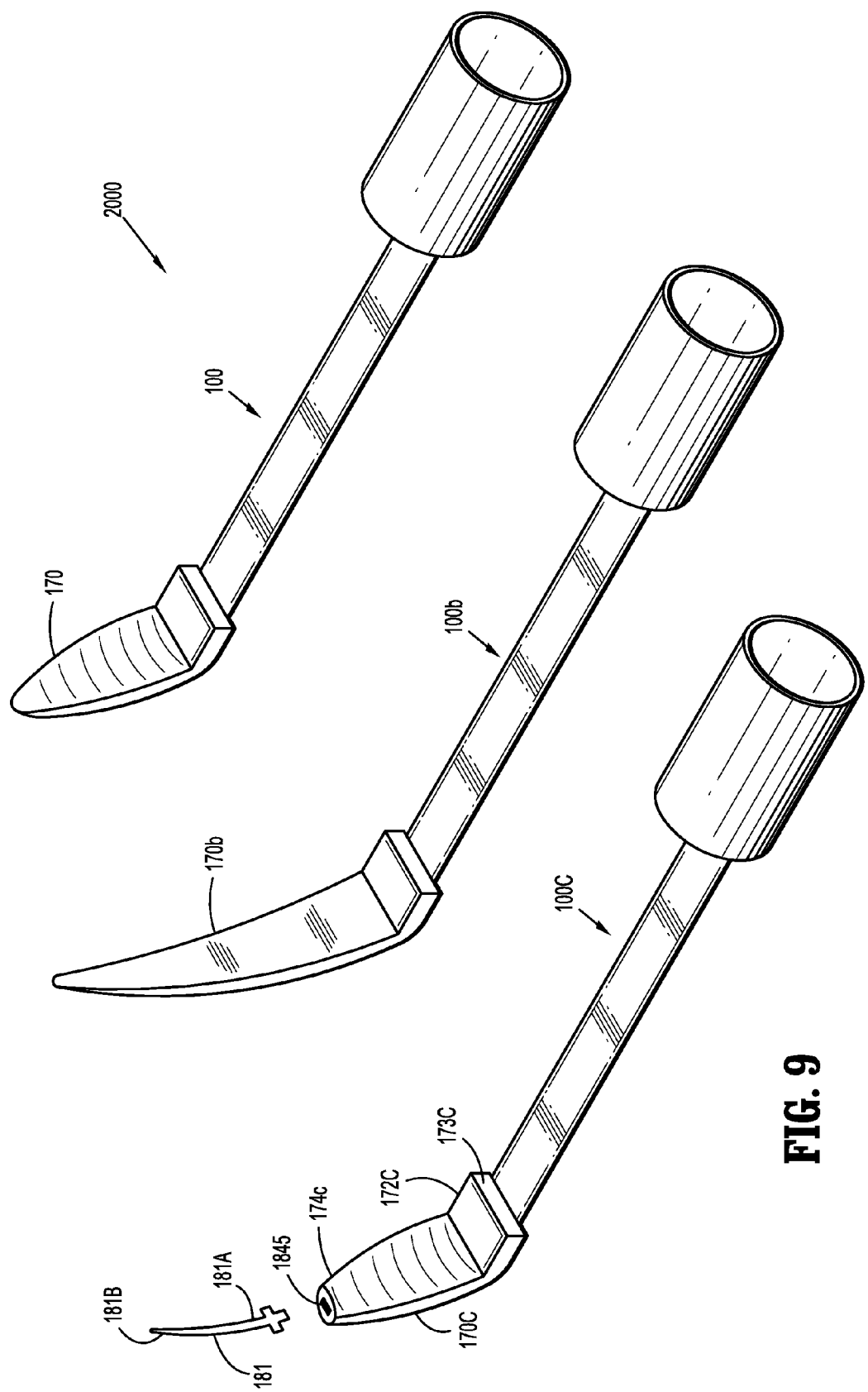
FIG. 9 is a perspective view illustrating a kit including multiple introducer assemblies having different tips in accordance with an aspect of a present disclosure.

Turning now to FIGS. 8 and 9, introducer assembly kits are illustrated and will be described below. As illustrated in FIG. 8, kit 1000 includes introducer assembly 100c and interchangeable dissecting devices 181a, 181b, and 181c. Although shown as including interchangeable dissecting devices 181a, 181b, and 181c, it is envisioned that kit 100c may include more or fewer interchangeable dissecting devices. Each of interchangeable dissecting devices 181a, 181b, and 181c include an attachment structure 184 for coupling the interchangeable dissecting devices 181a, 181b, and 181c to tip 170c of introducer assembly 100c. During use, a user may select one of interchangeable dissecting devices 181a, 181b, and 181c for attachment to introducer assembly 100c that best suits the user's needs, prior to, or subsequent to, releasably coupling the introducer assembly 100c to an end effector 20 (see e.g., FIGS. 4A-4B).

Turning now to FIG. 9, another aspect of a kit is illustrated and described as kit 2000. Kit 2000 includes introducer assemblies 100, 100b, and 100c. Although illustrated and described as including introducer assemblies 100, 100b, and 100c, it is envisioned that kit 2000 may include more or fewer introducer assemblies, such as introducer assembly 100d and/or introducer assembly 100e. Introducer assembly 100b is similar to introducer assembly 100, except introducer assembly 100b includes tip 170b which has a different configuration from tip 170. For example, tip 170b may have a more elongated configuration, larger size, different shape, sharper edge, different composition, or may be more rigid or flexible and/or elastomeric than tip 170. In aspects, kit 2000 further includes at least one interchangeable dissecting device 181 to be used with introducer assembly 100c. During use, a user may select one of introducer assemblies 100, 100b, and 100c to releasably couple to end effector 20 (see e.g., FIGS. 4A-4B) prior to performing any dissection.

It is noted that although not described in detail, end effector 20 preferably is adapted to access the surgical site through a trocar cannula assembly as is known in the art. To accomplish this, anvil member 28 and surgical fastener cartridge 34 (or first jaw 24 and second jaw 26) are maintained in a clamped position as elongated shaft 18 and end effector 20 are inserted through the cannula (not shown). In aspects, introducer assembly 100, and in particular tip 170, does not extend below a plane defined by a bottom surface surgical fastener cartridge 34, nor does body portion 150 extend outwardly beyond the sidewalls of anvil member 28. As such, surgical fastener applying apparatus 10 including introducer assembly 100 may be used with a trocar cannula assembly sized to receive a surgical stapling device not having an introducer assembly attached to the surgical device.

Persons skilled in the art will understand that the devices and methods specifically described herein and illustrated in the accompanying figures are non-limiting exemplary aspects, and that the description, disclosure, and figures should be construed merely exemplary of particular aspects. It is to be understood, therefore, that the present disclosure is not limited to the precise aspects described, and that various other changes and modifications may be effected by one skilled in the art without departing from the scope or spirit of the disclosure. Additionally, it is envisioned that the elements and features illustrated or described in connection with one exemplary aspect may be combined with the elements and features of another without departing from the scope of the present disclosure, and that such modifications and variations are also intended to be included within the scope of the present disclosure. Accordingly, the invention is not to be limited by what has been particularly shown and described, except as indicated by the appended claims.

What is claimed is:

1. A dissecting kit for use with a surgical instrument, comprising:
an introducer assembly configured to couple to an end effector of the surgical instrument having first and second jaws, the introducer assembly comprising:
a cylindrical collar configured to slidably engage a portion of the end effector of the surgical instrument;
a tip having proximal and distal portions, the proximal portion of the tip including an opening configured to receive a distal end of the surgical instrument therein, the distal portion of the tip having an attachment structure; and
an elongated body portion extending between the collar and the tip; and
at least one dissecting device releasably attachable to the attachment structure of the tip.

2. The dissecting kit of claim 1, wherein the opening is deformable in shape such that the proximal portion of the tip conforms to a shape and size of the distal end of the surgical instrument.

3. The dissecting kit of claim 1, wherein at least a portion of the tip is coated with an epoxy.

4. The dissecting kit of claim 1, wherein the introducer assembly is at least partially formed from an elastomeric material.

5. The dissecting kit of claim 1, wherein the collar, the body portion, and the tip are monolithically formed.

6. The dissecting kit of claim 1, wherein the collar is tapered such that an inner diameter of a proximal portion of the collar is larger than an inner diameter of a distal portion of the collar.

7. A dissecting kit for use with a surgical instrument, comprising:
an introducer assembly configured to couple to an end effector of the surgical instrument having first and second jaws, the introducer assembly comprising:
a first cylindrical collar configured to releasably engage the surgical instrument; and
a first tip having an opening configured to receive a distalmost end of the surgical instrument therein;
a second introducer assembly comprising:
a second collar configured to releasably engage the surgical instrument; and
a second tip having an opening configured to receive a distalmost end of the surgical instrument therein, the first tip and second tip having different shapes; and
a third introducer assembly comprising:
a third collar configured to releasably engage the surgical instrument;
a third tip having an opening configured to receive a distalmost end of the surgical instrument therein, the third tip configured to releasably receive a dissecting device; and
a plurality of dissecting devices, each dissecting device of the plurality of dissecting devices configured to be releasably coupled to the third tip.

8. The dissecting kit according to claim 7, wherein the introducer assembly further includes an illuminating element at a distal portion of the first tip.

9. The dissecting kit according to claim 7, wherein the introducer assembly further includes an imaging element at a distal portion of the first tip.

10. A dissecting kit for use with a surgical instrument, comprising:
an introducer assembly configured to couple to an end effector of the surgical instrument having first and second jaws, the introducer assembly comprising:
a collar configured to slidably engage a portion of the end effector of the surgical instrument;
a tip having proximal and distal portions, the proximal portion of the tip including an opening configured to receive at least one of a distal portion of the first jaw or a distal portion of the second jaw, the distal portion of the tip having an attachment structure; and
an elongated body portion extending between the collar and the tip; and
at least one dissecting device releasably attachable to the attachment structure of the tip, wherein the collar is tapered such that an inner diameter of a proximal portion of the collar is larger than an inner diameter of a distal portion of the collar.

* * * * *